United States Patent [19]

Siegel et al.

[11] Patent Number: 4,647,575

[45] Date of Patent: Mar. 3, 1987

[54] N-BICYCLOHEPTYL-AND N-BICYCLOHEPTENYL-IMIDAZOLES FOR AFFECTING SERUM LIPOPROTEINS

[75] Inventors: Herbert Siegel; Ernold Granzer, both of Kelkheim, Fed. Rep. of Germany

[73] Assignee: Hoechst Aktiengesellschaft, Fed. Rep. of Germany

[21] Appl. No.: 714,021

[22] Filed: Mar. 20, 1985

[30] Foreign Application Priority Data

Mar. 22, 1984 [DE] Fed. Rep. of Germany ....... 3410498

[51] Int. Cl.$^4$ ................... A61K 31/415; C07D 233/60
[52] U.S. Cl. ................... 514/396; 514/399; 548/341; 548/346
[58] Field of Search ............... 548/341, 346; 514/399, 514/396

[56] References Cited

U.S. PATENT DOCUMENTS 3,682,951  8/1972  Kreider .............................. 548/341

FOREIGN PATENT DOCUMENTS 0064245  1/1982  European Pat. Off. ............ 548/335
2944663  5/1981  Fed. Rep. of Germany ...... 548/335

OTHER PUBLICATIONS

March J., *Advanced Organic Chemistry*, McGraw Hill, New York, 1968, pp. 343–344.
Baggaley et al., *J. Med. Chem.* 18, 833 (1975).

Primary Examiner—Richard A. Schwartz
Attorney, Agent, or Firm—Finnegan, Henderson, Farabow, Garrett & Dunner

[57] ABSTRACT

N-Bicycloheptyl- and N-bicycloheptenyl-imidazoles of the formula I

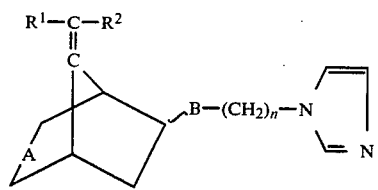

in which A, B, $R^1$, $R^2$ and n have the indicated meanings, and their physiologically tolerated salts, a process for the preparation of these compounds, pharmaceutical products based on these compounds, and their use as medicaments, in particular for the treatment of disturbances of the serum lipoprotein spectrum, are the subject-matter of the invention.

4 Claims, No Drawings

N-BICYCLOHEPTYL-AND N-BICYCLOHEPTENYL-IMIDAZOLES FOR AFFECTING SERUM LIPOPROTEINS

The invention relates to N-bicycloheptyl- and N-bicycloheptenyl-imidazoles, a process for their preparation, pharmaceutical products containing these compounds, and their use as medicaments, in particular for the treatment of hyperlipidemia.

It has already been described that imidazoles which are substituted on the nitrogen atom by a straight-chain or branched alkyl radical or by the benzyl radical have a hypolipidemic effect (see J. Med. Chem. 18, 833 (1975)). However, in order to achieve therapeutically satisfactory results, high doses of the compounds described in this publication are necessary. Imidazolmethylsubstituted bicycles having an antithromboembolic effect are described in German Offenlegungsschrift No. 2,944,663. Where the bicycles mentioned in this publication are bicycloheptanes, they are unsubstituted in the 7-position.

It has been found, surprisingly, that N-bicycloheptyl- and N-bicycloheptenyl-imidazoles substituted in the 7-position have a much greater hypolipidemic effect than imidazole derivatives hitherto described.

Thus the invention relates to new N-bicyclopheptyl- and N-bicycloheptenyl-imidazoles of the formula I

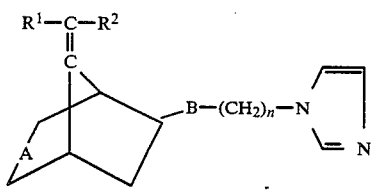

in which
  $R^1$ and $R^2$ are identical or different and denote alkyl having 1 to 10 carbon atoms, cycloalkyl having 4 to 10 carbon atoms, phenyl which is optionally mono- or disubstituted by halogen, $(C_1-C_4)$-alkyl, $(C_1-C_4)$-alkoxy, trifluoromethyl, hydroxyl, amino, $(C_1-C_4)$-alkylamino or $(C_1-C_4)$-dialkylamino, the substituents in the case of disubstitution being identical or different, naphthyl or phenylalkyl having 1 to 4 alkyl carbon atoms, or
  $R^1$ and $R^2$ together represent a $(CH_2)_m$ bridge which is optionally substituted by phenyl, m denoting a number from 3 to 10,
  A represents a single or double bond,
  B denotes a single bond or, if n represents 0 or 1, also the

group or, if n represents 1, the —CHOH— group, and
  n represents 0, 1, 2, 3 or 4,
and to their physiologically tolerated acid addition salts.

Alkyl is to be understood to be both straight-chain and branched alkyl.

The wavy line in formula I and in the formulae which follow indicates that the substituents can be in either the endo- or exo-position on the bicycle.

Preferred compounds of the formula I are those in which $R^1$ and $R^2$ are identical or different and denote phenyl and phenyl which is monosubstituted by halogen, in particular fluorine or chlorine. A preferably represents a single bond, n particularly denotes 0 to 1, and B a single bond or the —CO— group.

The process for the preparation of compounds of the formula I and their salts comprises (a) converting an alcohol of the formula II

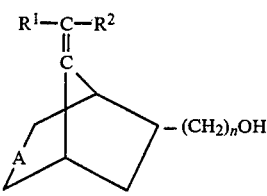

in which A, $R^1$, $R^2$ and n have the meanings indicated for formula I, by methods known per se into a compound of the formula III

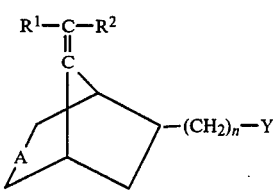

in which A, $R^1$, $R^2$ and n have the meanings indicated for formula I, and Y denotes a leaving group, such as, for example, hydrogen, in particular chlorine or bromine, or a sulfonic acid derivative, such as $(C_1-C_4)$-alkyl-$SO_2$—O—,

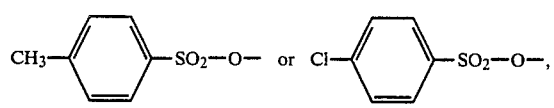

and reacting the latter with imidazole or an imidazole salt of the formula IV

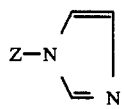

in which Z denotes hydrogen or alkali metal, to give a compound of the formula I in which $R^1$, $R^2$, A and n have the meanings indicated, and B represents a single bond, and, where appropriate, hydrogenating the double bond in a resulting compound in which A represents a double bond, the hydrogenation being carried out either on an intermediate or on a compound of the formula I (A=double bond), or (b) reacting a halide of the formula V

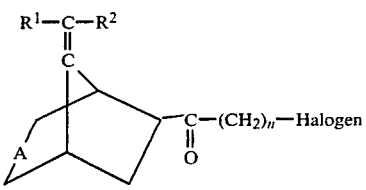

in which A, $R^1$ and $R^2$ have the meanings indicated for formula I, n represents 0 or 1, and halogen represents bromine or chlorine, with imidazole or an imidazole salt of the formula IV, to give a compound of the formula I in which A, $R^1$ and $R^2$ have the meanings indicated, B is the

group, and n is 0 or 1, and, where appropriate, reducing the latter to give a compound in which B denotes the CHOH group and, if desired, converting with an acid the compounds obtained by (a) or (b) into the physiologically tolerated acid addition salts.

In process (a), the alcohols of the formula II are converted into the halogen compound III (Y=halogen), for example with an inorganic halide, such as, for example, $POCl_3$, $PCl_3$, $PBr_3$, $P(C_6H_5)_3/CCl_4$ or $SOCl_2$, or they are converted into the sulfonic esters with a sulfonyl halide. Suitable sulfonyl halides are the customarily used halides, such as mesyl chloride, tosyl chloride or p-chlorobenzenesulfonyl chloride. The substitution of the halide or sulfonic ester is advantageously carried out with imidazole in the presence of an acid-binding additive, such as an aliphatic or aromatic amine, or with the sodium salt of imidazole, in a polar solvent, such as DMF, DMSO, THF or alcohol, at temperatures between 0° and 100° C.

The alcohols of the formula II are either described in the literature or are prepared in analogy to described methods. For the preparation of alcohols of the formula II in which n is 1, the procedure is advantageously as follows:

Bicycloheptene derivatives are obtained from $R^1$, $R^2$-substituted pentafulvenes and appropriately substituted olefins, such as, for example, acrylic acid, acrylic esters, acrylonitrile, α-chloroacrylonitrile, methyl vinyl ketone and other electron-poor olefins, without a solvent or in the presence of a solvent, at temperatures of, advantageously, 20°–80° C., in accordance with the method indicated in Ann. 566, pages 1 et seq. and 27 et seq. (1950). The bicycloheptene derivative of the formula VI

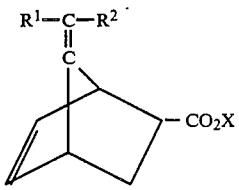

in which $R^1$ and $R^2$ have the meanings indicated, and X denotes hydrogen or a ($C_1$–$C_4$)-alkyl group, is obtained by reaction with acrylic acid or an appropriate acrylic ester. The reaction is many times faster than indicated in Ann. 566, 1 et seq. The reaction time is usually between a few hours and some days.

The fulvenes used to synthesize the bicycle are obtained by methods known from the literature (see Adv. in Alicyclic Chem. 2, 59 (1968)).

The compounds of the formula VI are particularly suitable for procedure (a). They are converted into the corresponding alcohol using a reducing agent, for example a complex hydride, such as $LiAlH_4$.

An alcohol of the formula II in which n is 1 and A represents a single bond is obtained by hydrogenation by methods known per se.

In the preparation of the alcohols of the formula II in which n represents O and A represents a single bond, the starting material used is, for example, a ketone of the formula VII

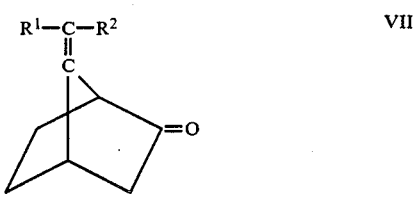

which is reduced, for example, with $LiAlH_4$ to give the desired alcohol.

Compounds of the formula VIII

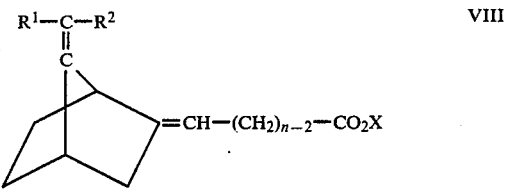

in which X denotes the cation of an alkali metal or ($C_1$–$C_4$)-alkyl are obtained by reaction of the same ketone VII with organometallic reagents, such as $(EtO)_2$-POCHNaCOX, or with a Wittig reagent such as, for example, $(C_6H_5)_3P=CH-(CH_2)_{n-2}-COX$. The reduction to give the alcohol is carried out as described above, for example. In the subsequent hydrogenation, only the double bond in the side-chain is hydrogenated.

In principle, the hydrogenation of the endocyclic double bond (A=double bond) is possible at any stage of the synthetic sequence. However, it is preferably carried out at the stage of the cyclo adduct (compound of the formula VI) or on the imidazole derivative I itself. The procedure is known per se, the catalyst used being, for example 5% Pd on charcoal. In this way, compounds according to the invention, with A=single bond, are obtained.

The preparation of compounds of the formula I which contain a keto or hydroxyl group in the imidazolesubstituted side-chain (B=CO or CHOH) is carried out by process (b). The halide of the formula V used as starting material is obtained by methods known from the literature. The methyl ketone which is described in Ann. 566, 27 (1950), which is preferably used, was converted under kinetic control into the silyl enol ether (see JOC 34, 2324 (1969)) and the latter was then brominated (see Synthesis 1976, 194).

The imidazole derivative according to the invention is obtained by reacting the corresponding halide, preferably in a polar organic solvent, such as DMF, DMSO, THF or low molecular weight alcohols, at a temperature between 0° and 100° C., preferably room temperature, with at least twice the amount of imidazole or the Na salt of imidazole. The resulting keto imidazole derivative (B=CO) can, where appropriate, be reduced to the corresponding alcohol (B=CHOH). Complex hydrides such as, for example $LiAlH_4$ or $NaBH_4$, in a suitable solvent are most suitable for the reduction.

Acid addition salts can be prepared from the imidazole derivatives of the general formula (I), which usually result as an oil. All acids which form physiologically tolerated salts are suitable for this. These include both inorganic acids such as, for example, hydrochloric acid, nitric acid and sulfuric acid and mono- and bifunctional organic acids, in particular carboxylic acids, such as acetic acid, succinic acid, tartaric acid etc.

The compounds according to the invention, of the formula I, have valuable pharmacological properties, in particular they exhibit a very strong and favorable effect on the serum lipoproteins. Thus the invention also relates to pharmaceutical products based on these compounds, and to their use as medicaments, in particular for affecting the serum lipoproteins.

It is generally accepted that hyperlipoproteinemia is an essential risk factor for the development of arteriosclerotic vascular changes, in particular coronary heart disease. Thus, extreme importance attaches to the reduction in raised serum lipoproteins for the prophylaxis and reduction of arteriosclerotic changes. However, very particular classes of serum lipoproteins are important in this context, since the low density (LDL) and very low density lipoproteins (VLDL) represent a risk factor for atherogenesis, while the high density lipoproteins (HDL) exert a protective function with respect to arteriosclerotic vascular changes. Accordingly, hypolipidemic agents should lower VLDL-cholesterol and LDL-cholesterol in the serum but, at the same time, where possible leave the HDL-cholesterol concentration unaffected or even raise it, so that the antiatherogenic index (HDL/LDL) increases.

The compounds according to the invention have valuable therapeutic properties. Thus, they lower, in particular, the concentration of LDL and VLDL but they lower the HDL fraction only at excessive doses which have already reduced the LDL-cholesterol concentration by more than about 50%, so that the result in the therapeutically utilizable range is a great reduction in the LDL fraction without any effect on the HDL fraction. Thus, these compounds represent a considerable advance compared with the comparison compound clofibrate which, apart from LDL, always brings about a very great reduction in HDL, as is evident from the data described below. Thus they can be used for the prophylaxis and regression of arteriosclerotic changes since they eliminate a causal risk factor.

This includes not only primary hyperlipidemia, but also certain types of secondary hyperlipidemia as occur with, for example, diabetes. The increase in the relative liver weight caused by the compounds at effective doses is zero or only slight, while clofibrate, which is used as a standard hypolipidemic agent, leads to a great increase in the relative liver weight.

The effect of the compounds listed was investigated on the serum lipoproteins in male Wistar rats which were treated with the compounds listed, suspended in polyethylene glycol 400, by gavage for 7 days. In addition, a control group received only the solvent polyethylene glycol 400, and, in most experiments, there was a group of rats which received the standard hypolipidemic agent clofibrate. As a rule, 10 animals were used in each group, their blood being sampled from the orbital plexus after shallow ether anesthesia at the end of the treatment. The serum lipoproteins from the rat serum obtained were fractionated into the following density classes in a preparative ultracentrifuge:

VLDL<1.006; LDL 1.006 to 1.04; HDL 1.04 to 1.21

Since, in contrast to humans, the serum lipoproteins of the rat contain about 4/5 HDL-cholesterol and only 1/5 LDL-cholesterol, and only very small amounts of VLDL (conversely, about 4/5 LDL and VLDL and only 1/5 HDL in humans), fractionation of the rat serum into lipoprotein classes is absolutely necessary for assessment of a hypolipidemic effect in the rat. This is because simply reducing the serum total cholesterol content in the rat would merely indicate the undesired reduction in the antiatherogenic HDL class which predominates in the rat. A desired reduction of LDL with, at the same time, a desired increase in HDL would, however, have no (substantial) effect on the total cholesterol content of rat serum.

The cholesterol contained in the lipoprotein fractions isolated in the ultracentrifuge was determined completely enzymatically by the CHOD-PAP method using the Boehringer-Mannheim assay combination, and the figures have been converted into $\mu g/ml$ serum. Table I below shows the percentage change in the lipoprotein cholesterol in the treated group compared with a control group kept under the same conditions. As is evident from Table I, clofibrate brings about a greater reduction in the HDL than in the LDL fraction, while the new compounds exert a strong and selectively reducing effect on the atherogenic lipoprotein fractions (VLDL and LDL), and leave the protective HDL fraction essentially unaffected.

TABLE I

Percentage changes in the Lipoproteins in rat serum after oral administration of the compounds for 7 days

| Example No. | Dose mg/kg/day | % change in cholesterol, relative to the control groups | | | | | % change in the relative liver weight |
|---|---|---|---|---|---|---|---|
| | | in serum | in the serum Lipoprotein fractions | | | | |
| | | | VLDL | LDL | HDL | HDL | |
| 17 | 30 | −55 | | −88 | −54 | 3.74 | +20 |
| | 12.5 | −47 | | −82 | −39 | 3.34 | +10 |
| | 5 | −26 | | −43 | −17 | 1.46 | +3 |
| | 3 | +2 | | −26 | +2 | 1.38 | +4 |
| | 1 | −13 | −60 | −23 | −11 | 1.16 | |
| | 0.3 | +6 | +13 | −26 | −2 | 1.33 | −1 |
| 15 | 30 | −78 | −74 | −94 | −95 | 0.93 | +31 |
| | 10 | −96 | −88 | −100 | −98 | | +24 |

TABLE I-continued

Percentage changes in the Lipoproteins in rat serum after oral administration of the compounds for 7 days

| Example No. | Dose mg/kg/day | % change in cholesterol, relative to the control groups | | | | | % change in the relative liver weight |
|---|---|---|---|---|---|---|---|
| | | in serum | in the serum Lipoprotein fractions | | | | |
| | | | VLDL | LDL | HDL | HDL | |
| | 3 | −93 | −63 | −89 | −96 | 0.35 | +24 |
| | 1 | −80 | 0 | −89 | −83 | 1.49 | +19 |
| | 0.3 | −53 | +19 | −69 | −58 | 1.37 | +6 |
| | 0.1 | −2 | −20 | −36 | −9 | 1.43 | +1 |
| | 0.03 | +1 | −33 | −21 | −5 | 1.78 | −1 |
| 7 | 3 | −11 | −18 | −30 | −4 | 1.36 | −1 |
| 2 | 30 | +7 | −31 | −37 | +11 | 1.76 | +15 |
| 22 | 10 | −5 | −57 | −44 | +4 | 1.85 | +10 |
| | 3 | −5 | −57 | −29 | 0 | 1.42 | 0 |
| 4 | 10 | −69 | +50 | −88 | −74 | 2.13 | +10 |
| | 3 | −36 | −5 | −53 | −36 | 1.36 | 0 |
| | 1 | −15 | +6 | −36 | −19 | 1.0 | +1 |
| 20 | 3 | −46 | 0 | −75 | −50 | 2.6 | +2 |
| | 0.3 | −2 | −9 | −30 | −9 | 1.30 | −4 |
| 21 | 0.3 | −18 | −20 | −25 | −16 | 1.12 | 0 |
| 9 | 30 | −12 | −43 | −40 | −14 | 1.43 | +10 |
| 14 | 3 | −14 | +32 | −44 | −9 | 0.97 | 0 |
| 12 | 0.3 | −15 | −10 | −25 | −14 | 1.16 | 0 |
| 13 | 0.3 | −17 | −10 | −37 | −17 | 1.33 | −2 |
| 24 | 0.1 | −49 | −6 | −68 | −40 | 1.84 | +12 |
| 25 | 3 | −16 | −17 | −36 | −11 | 1.39 | +2 |
| | 0.3 | −2 | +10 | −16 | +3 | 1.23 | +8 |
| Clofibrate | 100 | −26 | −10 | −38 | −23 | 1.18 | +29 |

Particularly suitable therapeutic preparations of the compounds of the formula I are tablets, coated tablets, capsules, suppositories and syrups. In these, the new compounds can be used either alone or mixed with pharmacologically acceptable vehicles. An oral administration form is preferred. For this purpose, the active compounds are preferably mixed with auxiliaries known per se, and converted, by methods known per se, into suitable administration forms, such as tablets, hard gelatine capsules, aqueous or oily suspensions or aqueous or oily solutions. Examples of inert vehicles which can be used are magnesium carbonate, lactose or corn starch, with the addition of other substances such as, for example, magnesium stearate. This can entail the preparation being carried out as dry or as moist granules. Particularly suitable oily vehicles or solvents are vegetable and animal oils such as, for example, sunflower oil or fish liver oil. A suitable daily dose is about 20 mg to 1 g, preferably 50 to 100 mg. A dosage unit preferably contains 10 to 25 mg.

For the treatment of disturbances of lipid metabolism, apart from the customary fillers and vehicles, the formulations can also contain an antihypertensive agent such as, for example, a saluretic, reserpine, hydralazine, guanethidine, α-methyldopa, clonidine or a β-sympathicolytic agent, a compound having antithrombotic activity, such as, for example, acetylsalicylic acid, sulfinpyrazone, ticlopidine and heparinoids, or an agent having antihyperuricemic activity, an oral antidiabetic, a geriatric agent or an agent effecting an increase in blood flow.

The examples which follow illustrate the preparation of the compounds:

Unless otherwise specified, the NMR spectra were recorded in $DCCl_3$. The chemical shifts are expressed in $\delta$ values.

EXAMPLE 1 exo,endo-2-(1-Imidazolomethyl)-7-isopentylidenebicyclo[2.2.1]heptane (a) Methyl exo,endo-7-isopentylidenebicyclo[2.2.1]-hept-5-ene-2-carboxylate 23.3 g (0.175 mol) of 6,6-diethylfulvene are mixed with 2.4 g (0.280 mol) of methyl acrylate, a spatula tip of hydroquinone is added, and the mixture is heated at 60° C. for 30 h. After removal of the excess acrylate in vacuo, 30.7 g of methyl exo,endo-7-isopentylidenebicyclo[2.2.1]hept-5-ene-2-carboxylate are obtained as an oil.

NMR: 6.0–6.5, m, 2H; 3.6 and 3.7 s, exo and endo $CO_2CH_3$; 1.2–3.5 m, 9H; 0.9, t, $2CH_3$ (b) Methyl exo,endo-7-isopentylidenebicyclo[2.2.1]heptane-2-carboxylate 30.6 g (0.138 mol) of ester from (a) are dissolved in 100 ml of THF. After addition of 2 g of Pd/C, hydrogenation is carried out at room temperature and under atmospheric pressure until one equivalent of hydrogen has been absorbed. After filtering off the catalyst with suction, the filtrate is distilled at 0.2 mm. 20.1 g of methyl exo,endo-7-isopentylidenebicyclo[2.2.1]heptane-2-carboxylate of boiling point 76° C. are obtained.

NMR: 3.6 and 3.7, s, exo and endo $CO_2CH_3$; 0.7–3.0, m, 19H.

(c) exo,endo-2-Hydroxymethyl-7-isopentylidenebicyclo[2.2.1]heptane 1.9 g (50 mmol) of $LiAlH_4$ in 100 ml of absolute ether are initially introduced. Then, under gentle reflux, 20.0 g (90 mmol) of ester from (b) in 50 ml of absolute ether are added dropwise, and the mixture is then stirred under reflux for one hour. It is hydrolyzed with dilute hydrochloric acid, and the ether phase is separated off, washed with water and dried over sodium sulfate. After removal of the ether in vacuo, 15.7 g of the alcohol remain as an oil.

NMR: 3.6 and 3.2 d, exo and endo CH₂OH; 1.2–2.8, m, 13H; 0.9, t, 2CH₃.

(d) exo,endo-7-Isopentylidenebicyclo[2.2.1]heptane-2-methyl(p-chlorophenyl)sulfonate 9.0 g (90 mmol) of triethylamine are added dropwise to 15.6 g (81 mmol) of alcohol from (c) and 18.8 g (89 mmol) of p-chlorobenzenesulfonyl chloride in 100 ml of methylene chloride at room temperature. After 16 hours, water is added, and the organic phase is separated off, washed once with water and dried. After evaporation in a rotary evaporator, 26.6 g of exo,endo-7-isopentylidenebicyclo[2.2.1]heptane-2-methyl(p-chlorophenyl)sulfonate remain as an oil.

NMR: 7.4–8.1, m, 4H; 4.0, q and 3.6, d, exo and endo

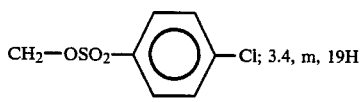 3.4, m, 19H (e) exo,endo-2-(1-Imidazolomethyl)-7-isopentylidenebicyclo[2.2.1]heptane 6.4 g (72 mmol) of sodium imidazolide in 80 ml of DMF are initially introduced, and 25.2 g (71 mmol) of sulfonic ester from (d) in 50 ml of DMF are added dropwise at room temperature. The reaction mixture is stirred at 60° C. for 16 h, then cooled and water is added. The mixture is extracted three times with 150 ml of methylene chloride each time, and the organic phase is dried and evaporated. After purification of the residue by column chromatography on silica gel using cyclohexane/ethyl acetate (2:1), 6 g of the title compound are obtained as a pale yellow, solidifying oil. Formula:

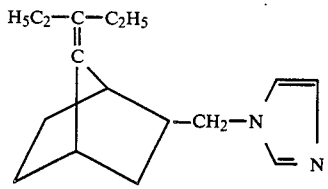

NMR: 7.4, s, 1H; 6.9, d, 2H; 3.9, d and 3.6, q, exo and endo CH₂-imidazole; 0.5–2.7 m, 19H.

EXAMPLE 2 endo-2-(1-Imidazolomethyl)-7-cyclohexylidenebicyclo[2.2.1]heptane 4 g (15.8 mmol) of endo-2-(1-imidazolomethyl)-7-cyclohexylidenebicyclo[2.2.1]hept-5-ene (prepared in analogy of Example 1(a), (c), (d), (e) from 6,6-pentamethylenefulvene, methyl acrylate and sodium imidazolide; melting point 48° C., see Example 10) are hydrogenated in 50 ml of THF at room temperature and under atmospheric pressure, in the presence of 0.5 g of Pd/c (5%), until one equivalent of hydrogen has been absorbed. The catalyst is then filtered off, the solution is evaporated, and the residue is recrystallized from isopropyl ether. 3.3 g of imidazole derivative of melting point 95° C. are obtained. Formula:

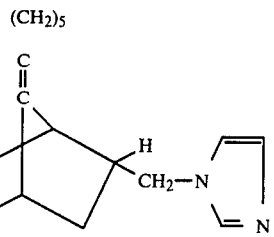

NMR: 7.5, s, 1H; 6.9, d, 2H; 3.9, d and 3.6, q, exo and endo CH₂-imidazole; 0.5–2.7, m, 19H.

EXAMPLE 3 exo-2-(1-Imidazolomethyl)-7-diphenylmethylenebicyclo[2.2.1]heptane (a) exo and endo 7-Diphenylmethylenebicyclo[2.2.1]hept-5-ene-2-carboxylic acid 50 g (0.218 mol) of 6,6-diphenylfulvene and 31.3 g (0.435 mol) of acrylic acid are intimately mixed and allowed to stand at room temperature for 14 days until decolorized. By fractional recrystallization of the solid white crude product with ethanol, first 35.3 g of the endo acid of melting point 190° C. are obtained. Evaporation of the mother liquor and recrystallization of the residue from cyclohexane provides 8.4 g of the exo acid of melting point 146° C.

NMR: (endo acid): 7.4–7.0, m, 10H; 6.48, q, 1H, 6.28, q, 1H; 3.7–3.9, m, 1H; 3.35–3.55, m, 1H; 3.2, dt, 1H, 2.22 o, 1H; 1.64, q, 1H.

NMR (exo acid): 7.0–7.4, m, 10H; 6.42 t, 2H; 3.54–3.64, m, 1H; 3.40–3.52, m, 1H; 2.20–2.55, m, 2H; 1.60, q, 1H.

(b) Methyl exo-7-diphenylmethylenebicyclo[2.2.1]hept-5-ene-2-carboxylate 7.4 g (24.3 mmol) of the exo acid from (a) are dissolved in 50 ml of absolute methanol, and 0.5 g of concentrated sulfuric acid is added. The mixture is stirred at 40° C. for 2 hours, allowed to stand at room temperature overnight, then water is added and the mixture is extracted with methylene chloride. After drying and evaporation of the organic phase, 7.8 g of methyl ester remain as a yellowish oil.

NMR: 6.9–7.4, m, 10H; 6.2–6.4, m, 2H; 3.2–3.8, m, 2H; 3.4, s, 3H of CO₂CH₃; 2.1–2.6, m, 2H; 1.2–1.8, m, 1H.

(c) Methyl exo-7-diphenylmethylenebicyclo[2.2.1]heptane-2-carboxylate 7.4 (23.3 mmol) of ester from (b) are dissolved in 100 ml of THF, and hydrogenation is carried out at room temperature and under atmospheric pressure, in the presence of 5% Pd on charcoal, until one equivalent of hydrogen has been absorbed. The catalyst is filtered off, and the solution is evaporated. 8.2 g of methyl exo-7-diphenylmethylenebicyclo[2.2.1]heptane-2-carboxylate remain as an oily residue.

NMR: 7.0–7.5, m, 10H; 3.4, s, 3H of CO₂CH₃; 1.0–2.8, m, 9H.

(d) exo-2-Hydroxymethyl-7-diphenylmethylenebicyclo[2.2.1]heptane 7.9 g (24.8 mmol) of ester from (c) in 50 ml of dry ether are added dropwise to 1.0 g (27.1 mmol) of lithium aluminum hydride in 35 ml of dry ether. The mixture is stirred under reflux for 2 hours, then dilute hydrochloric acid is added, and the organic phase is separated off, washed once with water, dried and the solvent is removed under waterpump vacuum. 7.1 g of the alcohol are obtained as an oil.

NMR: 6.7–7.4, m, 10H; 3.3, q, 2H, CH$_2$OH; 0.9–2.5, m, 9H.

(e) exo-7-Diphenylmethylenebicyclo[2.2.1]heptane-2-methyl(p-chlorophenyl)sulfonate 7.0 g (24.1 mmol) of alcohol from (d) and 5.7 g (26.6 mmol) of p-chlorobenzenesulfonyl chloride in 50 ml of methylene chloride are initially introduced. 2.7 g (26.6 mmol) of triethylamine are added dropwise to this at room temperature. After standing overnight, water is added, and the organic phase is separated off, washed once with water, dried and evaporated. 11.8 g of sulfonic ester remain as an oil.

NMR: 6.9–7.9, m, 14H; 3.8, q, 2H,

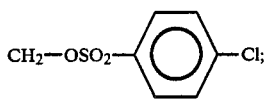

0.9–2.5, m, 9H.

(f) exo-2-(1-Imidazolomethyl)-7-diphenylmethylenebicyclo[2.2.1]heptane 10.9 g (23.5 mmol) of sulfonic ester from (e) in 25 ml of DMF are added to 2.3 g (25.8 mmol) of sodium imidazolide in 50 ml of DMF. The mixture is stirred at 50° C. for 5 hours, allowed to stand overnight, then water is added and the mixture is extracted three times with 150 ml of methylene chloride each time. The methylene chloride phase is washed once with water, dried and evaporated. The residue (7.2 g) is induced to crystallize with cyclohexane/ethyl acetate. 3.0 g of imidazole derivative of melting point 170° C. are obtained. Formula:

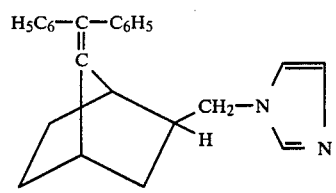

NMR: 7.1–7.5, m, 10H; 6.8, d, 2H; 6.4, s, 1H; 3.9, q, 2H; 1.0–2.6, m, 9H.

EXAMPLE 4 endo-2-(α-Keto-β-imidazoloethyl)-7-diphenylmethylenebicyclo[2.2.1]heptane 13.3 g (35 mmol) of endo-2-(bromoacetyl)-7-diphenylmethylenebicyclo[2.2.1]heptane (prepared in analogy to Ann. 566, 27 and Synthesis 1976, 194; the resulting crude product is used for the subsequent reaction) in 30 ml of DMF are added dropwise to 6.0 g (88 mmol) of imidazole in 150 ml of DMF, and the mixture is stirred at room temperature for 10 hours. Water is added, the mixture is extracted with methylene chloride, and the organic phase is washed once with water, dried and the solvent is removed in vacuo. 4.2 g of imidazole derivative are obtained as a pale yellow oil from the residue by column chromatography on silica gel. Formula:

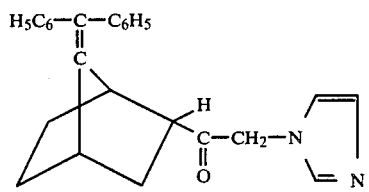

NMR: 6.0–7.4, m, 1H; 6.6, d, 2H, 4.5, s, 2H; 1.0–3.0, m, 9H.

EXAMPLE 5 exo,endo-2-(1-Imidazolyl)-7-diphenylmethylenebicyclo[2.2.1]heptane (a) exo,endo-2-Chloro-2-cyano-7-diphenylmethylenebicyclo[2.2.1]hept-5-ene 46 g (0.2 mol) of 6,6-diphenylfulvene and 17.6 g (0.2 mol) of α-chloroacrylonitrile are dissolved in 120 ml of toluene, and the solution is stirred at 80° C. for 20 hours. The solvent is removed under waterpump vacuum, and the residue is recrystallized from isopropanol. 37.2 g of exo,endo-2-chloro-2-cyano-7-diphenylmethylenebicyclo-[2.2.1]hept-5-ene are obtained as colorless crystals of melting point 135° C.

NMR: 7.0–7.4, m, 10H; 6.3–6.8, m, 2H; 3.8–4.0, m, 1H; 3.4–3.7, m, 1H; 2.9, q, 1H; 1.8, d, 1H.

(b) exo,endo-2-Chloro-2-cyano-7-diphenylmethylenebicyclo[2.2.1]heptane 17.5 g (55 mmol) of the bicycloheptene derivative from (a) are hydrogenated in the presence of 1 g of Pd/C, at room temperature and under atmospheric pressure, until 1235 ml of hydrogen have been absorbed. After filtering off the catalyst and removal of the solvent, 17.6 g of bicycloheptane derivative remain as a solid of melting point 84°–87° C.

NMR: 7.0–7.4, m, 10H; 1.3–3.2, m, 8H.

(c) 7-Diphenylmethylenebicyclo[2.2.1]heptan-2-one 17.5 g (55 mmol) of the bicycloheptane derivative from (b) are dissolved in 170 ml of DMSO. 7.8 g (139.3 mmol) of KOH in 30 ml of water are added to this. The mixture is then stirred at room temperature for 3 hours. After addition of 800 ml of water, the mixture is extracted with methylene chloride, and the organic phase is dried and evaporated. The residue is recrystallized from isopropyl ether. 13.7 g of ketone of melting point 88° C. are obtained.

NMR: 7.0–7.4, m, 10H; 3.1–3.4, m, 2H; 1.5–2.5, m, 6H.

(d) exo,endo-7-Diphenylmethylenebicyclo[2.2.1]heptan-2-ol 12.0 g (44 mmol) of the ketone from (c) are dissolved in a mixture of 50 ml of ethanol and 30 ml of tetrahydrofuran, and reduced with 1.2 g (33 mmol) of NaBH$_4$ at room temperature for 5 hours. After addition of water, the mixture is extracted with methylene chloride. The organic phase is dried and evaporated. 11.8 g of the alcohol are obtained as an oil.

NMR: 7.0–7.4, m, 10H; 3.5–4.5, m, exo- and endo-2-H; 1.0–2.8, m, 8H.

(e) exo,endo-7-Diphenylmethylenebicyclo[2.2.1]heptan-2-methanesulfonate 4.8 g (48.0 mmol) of triethylamine are slowly added to 11.5 g (42.8 mmol) of the alcohol from (d) and 5.4 g (47.0 mmol) of methanesulfonyl chloride in 100 ml of methylene chloride, and the mixture is stirred at room temperature for 16 h. After addition of 500 ml of water, the organic phase is separated off, dried and evaporated. 14.7 g of sulfonic ester are obtained as an oil.

NMR: 7.0–7.4, m, 10H; 4.8–5.2, m, exo- and endo-2-H; 2.9, s, $CH_3$; 1.0–3.1, m, 8H.

(f) exo,endo-2-(1-Imidazolyl)-7-diphenylmethylenebicyclo[2.2.1]heptane

A solution of Na imidazolide in 50 ml of DMF is prepared from 3.1 g (45.7 mmol) of imidazole and 1.4 g (45.7 mmol) of 80% sodium hydride. 14.7 g (41.5 mmol) of the sulfonic ester from (e) in 50 ml of DMF is added dropwise to this solution, and the mixture is stirred at 100° C. for 7 days. After addition of water, the mixture is extracted with methylene chloride. The organic phase is dried and evaporated. The oily residue (12.7 g) is chromatographed on silica gel (mobile phase: cyclohexane ethyl acetate, 3:1). 1.2 g of the desired imidazole derivative is eluted as an oil from which, with hydrogen chloride in ether, 1.0 g of the corresponding salt, of melting point 160° C., is obtained. Formula:

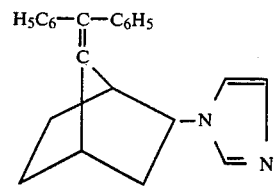

NMR: 8.8–9.0, s, 1H; 6.5–7.5, m, 13H; 5.4–5.7, m, 1H; 1.0–2.8, m, 8H.

The following compounds of the formula I are prepared in an analogous manner (Examples 6 to 23).

| No | $R^1$ | $R^2$ | A | B | Config. | n | phys. data |
|---|---|---|---|---|---|---|---|
| 6 | $CH_3$ | $CH_3$ | = | — | exo/endo | 1 | 158° C. (+HCl) |
| 7 | $CH_3$ | $CH_3$ | — | — | exo/endo | 1 | Oil, NMR: 7.4,s,1H;6.9,d,2H;3.9u,3.6 d, exo and endo-$CH_2$—Imidazole; 0.7–2.8,m,9H;2.7,s $CH_3$;2.6,d,$CH_3$ |
| 8 | $(CH_2)_4$ | | = | — | exo/endo | 1 | Oil, NMR: 7.4,s,1H;6.9,d,2H;6.0–6.5, m,2H;3.5–4.0,m,exo and endo-$CH_2$—Imidazole;0.5–3.1,m,13H |
| 9 | $(CH_2)_4$ | | — | — | exo/endo | 1 | Oil, NMR: 7.4,s,1H;6.9,d,2H;3.4–4.0, m,exo and endo-$CH_2$—Imidazole; 0.5–2.5,m,17H |
| 10 | $(CH_2)_5$ | | = | — | endo | 1 | 48° C. |
| 11 | $(CH_2)_2$—CH—$(CH_2)_2$ with $C_6H_5$ | | = | — | endo | 1 | 161° C. |
| 12 | $(CH_2)_2$—CH$(CH_2)_2$ with $C_6H_5$ | | — | — | endo | 1 | 130° C. |
| 13 | phenyl | phenyl | — | — | endo | 0 | 160° C. (+HCl) |
| 14 | phenyl | phenyl | = | — | endo | 1 | 140° C. |
| 15 | phenyl | phenyl | — | — | endo | 1 | 146° C. |
| 16 | phenyl | phenyl-Cl | — | — | endo | 1 | 165° C. (×HCl) |
| 17 | phenyl | phenyl-Cl | — | — | exo | 1 | 162° C. (+HCl) |
| 18* | phenyl | phenyl | — | CHOH | endo | 1 | 160° C. (+HCl) |

-continued

| No | R¹ | R² | A | B | Config. | n | phys. data |
|---|---|---|---|---|---|---|---|
| 19 | phenyl | 4-F-phenyl | — | — | exo | 1 | 210° C. (+HCl) |
| 20 | phenyl | 4-F-phenyl | — | — | endo | 1 | 144° C. |
| 21 | 4-F-phenyl | 4-F-phenyl | — | — | endo | 1 | 152° C. |
| 22 | 4-Cl-phenyl | 4-Cl-phenyl | — | — | endo | 1 | 198° C. (+HCl) |
| 23 | 4-Cl-phenyl | 4-Cl-phenyl | — | — | exo | 1 | Amorphous, NMR: 6.8–7.5,10H;6.4,s, 1H;3.5,q,2H,exo-CH₂—Imidazole; 0.7–2.8,m,9H. |

*was obtained by reduction of the compound from Example 4 with NaBH in a manner known per se.

For compounds 16, 17, 19 and 20, it is also possible for R² to be unsubstituted and R¹ to be phenylsubstituted by chlorine or fluorine.

EXAMPLE 24 exo-2-Carbonylimidazolyl-7-diphenylmethylenebicyclo[2.2.1]heptane (a) exo-7-Diphenylmethylenebicyclo[2.2.1]heptane-2-carboxylic acid 8 (26.5 mmol) of exo-7-diphenylmethylenebicyclo[2.2.1]hept-5-ene-2-carboxylic acid were dissolved in 80 ml of tetrahydrofuran and hydrogenated under atmospheric pressure and at room temperature, in the presence of 1 g of Pd/C, until one equivalent of hydrogen had been absorbed. After filtering off the catalyst and evaporation of the solution, 8.1 g of the hydrogenated acid remained as an oil.

NMR: 11.2, 1H; 6.9–7.4, m, 10H; 3.5–3.8, m, 2H; 1.0–3.2, m, 7H.

(b) exo-2-Carbonylimidazolyl-7-diphenylmethylenebicyclo[2.2.1]heptane 8.1 g (26.5 mmol) of the acid from (a) in 60 ml of tetrahydrofuran were initially introduced. 2 drops of pyridine were added, and 5.5 g (46 mmol) of thionyl chloride were added dropwise. The mixture was heated to reflux for two hours, the solvent was removed in vacuo, and 9.4 g of crude acid chloride were obtained. This was dissolved again in 50 ml of tetrahydrofuran and, at 0°–5° C., 6.9 g (102 mmol) of imidazole in tetrahydrofuran were added dropwise, and the mixture was stirred at room temperature for 24 hours and worked up with water and methylene chloride. 8.8 g of oil were obtained and distilled in a Kugelrohr (250° C., 0.3 mbar). 4.5 g of pure imidazole derivative were thus obtained. Formula:

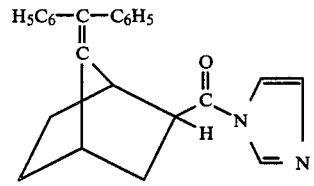

NMR: 8.1, s, 1H; 6.8–7.5, m, 10H; 3.2–3.8, m, 1H; 1.0–3.0, m, 8H.

EXAMPLE 25 exo,endo-2-(1-Imidazoloethyl)-7-diphenylmethylenebicyclo[2.2.1]heptane (a) Ethyl E,Z-7-diphenylmethylenebicyclo[2.2.1]heptane-2-methylenecarboxylate 3.0 g (0.1 mol) of 80% sodium hydride in 250 ml of dimethoxyethane were initially introduced, and 22.5 g (0.1 mol) of triethyl phosphonoacetate in dimethoxyethane were added dropwise. After one hour, 27.5 g (0.1 mol) of ketone obtained according to Example 5(c), in dimethoxyethane, were added dropwise, and the mixture was then stirred at 50° C. for 3 hours and worked up with water/methylene chloride. 35 g of product were obtained as an oil.

NMR: 7.0–7.4, m, 10H; 5.6 and 5.8, m, 1H; 4.2, q, 2H; 3.3, m, 1H; 1.0–3.0, m, 7H; 1.3, t, 3H.

(b) E,Z-7-Diphenylmethylenebicyclo[2.2.1]heptane-2-(ethyliden-2-ol)

23 g (0.067 mol) of ester from (a), in THF were added dropwise to 3.8 g (0.1 mol) of lithium aluminum hydride in 100 ml of THF, and the mixture was stirred at 70° C. for 8 hours and worked up with dilute hydrochloric acid/methylene chloride. After removal of the solvent, 21.6 g of crude product remained, from which 12.5 g of alcohol were isolated by column chromatography (silica gel, cyclohexane/ethyl acetate=5:1).

NMR: 7.0–7.4, m, 10H; 5.4–5.6, m, 1H; 4.1, d, 2H; 3.2, m, 1H; 2.9, m, 1H; 1.1–2.6, m, 6H.

(c) exo,endo-7-Diphenylmethylenebicyclo[2.2.1]heptane-2-(ethyl-2-ol)

6.8 g (22.5 mmol) of alcohol from (b) were dissolved in 100 ml of THF and hydrogenated in the presence of 1 g of Pd/C, at room temperature and under atmospheric pressure, until one equivalent of hydrogen had been absorbed. After filtering off the catalyst and removal of the solvent, 6.7 g of oil remained.

NMR: 6.9–7.4, m, 10H; 3.3–3.8, m, 1H; 0.5–3.1, m, 12H.

The alcohol from 25 (c) was reacted further to give the imidazole derivative in analogy to Example 3 e,f. 0.8 g of a colorless oil was obtained.

Formula:

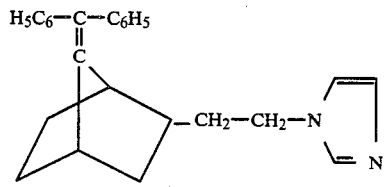

NMR: 6.6–7.5, m, 13H; 3.6–4.0, m, 2H; 0.6–2.8, m, 11H.

What is claimed is:

1. An N-bicycloheptyl- or N-bicycloheptenyl-imidazole of the formula I

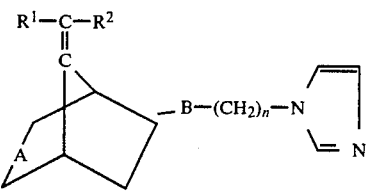

in which
$R^1$ and $R^2$ are identical or different and denote alkyl having 1 to 10 carbon atoms, cycloalkyl having 4 to 10 carbon atoms, phenyl which is optionally mono- or disubstituted by halogen, ($C_1$–$C_4$)-alkyl, ($C_1$–$C_4$)-alkoxy, trifluoromethyl, hydroxyl, amino, ($C_1$–$C_4$)-alkyl-amino or ($C_1$–$C_4$)-dialkylamino, the substituents in the case of disubstitution being identical or different, naphthyl or phenylalkyl having 1 to 4 alkyl carbon atoms, or
$R^1$ and $R^2$ together represent a $(CH_2)_m$ bridge which is optionally substituted by phenyl, m denoting a number from 3 to 10,
A represents a single or double bond,
B denotes a single bond or, if n represents 0 or 1, also the

group or, if n represents 1, the —CHOH— group, and
n represents 0, 1, 2, 3 or 4, or the physiologically tolerated acid addition salt thereof.

2. A compound as claimed in claim 1, wherein $R^1$ and $R^2$ in formula I are identical or different and denote phenyl, 4-chlorophenyl or 4-fluorophenyl, A denotes a single bond, n represents 0 or 1, and B denotes a single bond or the CO group.

3. A pharmaceutical composition for the treatment of disturbances of the serum lipoprotein spectrum containing an effective amount of a compound as claimed in claim 1 in a pharmacologically acceptable vehicle.

4. A process for the treatment of disturbances of the serum lipoprotein spectrum, which comprises administration to a mammal of an effective amount of a compound as claimed in claim 1.

* * * * *